(12) United States Patent
Agaoglu

(10) Patent No.: US 8,887,750 B2
(45) Date of Patent: Nov. 18, 2014

(54) DEVICE FOR REDUCING ELECTROMAGNETIC POLLUTION

(75) Inventor: Cemre Agaoglu, Ankara (TR)

(73) Assignees: Cemre Agaoglu, Ankara (TR); Demet Agaoglu, Ankara (TR)

( * ) Notice: Subject to any disclaimer, the term of this patent is extended or adjusted under 35 U.S.C. 154(b) by 0 days.

(21) Appl. No.: 14/008,643

(22) PCT Filed: Mar. 28, 2012

(86) PCT No.: PCT/IB2012/051471
§ 371 (c)(1),
(2), (4) Date: Dec. 9, 2013

(87) PCT Pub. No.: WO2012/131587
PCT Pub. Date: Oct. 4, 2012

(65) Prior Publication Data
US 2014/0182700 A1      Jul. 3, 2014

(30) Foreign Application Priority Data

Mar. 28, 2011   (TR) .............................. a 2011 02943

(51) Int. Cl.
| | |
|---|---|
| F16K 17/36 | (2006.01) |
| F16K 31/04 | (2006.01) |
| F16K 31/12 | (2006.01) |
| A61N 1/16 | (2006.01) |
| A61H 33/14 | (2006.01) |

(52) U.S. Cl.
CPC .......... *A61N 1/16* (2013.01); *A61H 2201/5058* (2013.01); *A61H 2033/143* (2013.01)
USPC ....... 137/78.1; 250/505.1; 137/78.5; 239/2.1; 422/105; 422/106; 422/107; 422/108; 422/120

(58) Field of Classification Search
USPC .......... 250/505.1, 515.1, 516.1, 517.1, 519.1; 137/78.1, 78.5; 239/2.1; 422/105–108
See application file for complete search history.

(56) References Cited

U.S. PATENT DOCUMENTS

| | | | | |
|---|---|---|---|---|
| 6,310,355 | B1 * | 10/2001 | Cadwalader | 250/515.1 |
| 6,369,399 | B1 * | 4/2002 | Smirnov | 250/515.1 |
| 7,815,820 | B2 * | 10/2010 | Tan et al. | 252/518.1 |
| 2013/0153795 | A1 * | 6/2013 | DeBaun | 250/515.1 |

FOREIGN PATENT DOCUMENTS

| | | |
|---|---|---|
| DE | 20014497 U1 | 12/2000 |
| DE | 102007049627 A1 | 4/2009 |
| EP | 2246030 A1 | 11/2010 |

* cited by examiner

*Primary Examiner* — Jack Berman
*Assistant Examiner* — Meenakshi Sahu
(74) *Attorney, Agent, or Firm* — Gokalp Bayramoglu

(57) ABSTRACT

The present invention relates to a device for reducing electromagnetic pollution (1) which measures the electromagnetic radiation amount in the environment, and enables to reduce radiation when the radiation amount exceeds a predetermined threshold value.

10 Claims, 2 Drawing Sheets

DEVICE FOR REDUCING ELECTROMAGNETIC POLLUTION

FIELD OF THE INVENTION

The present invention relates to a device which enables to absorb the electromagnetic radiations and to reduce electromagnetic pollution by this means.

BACKGROUND OF THE INVENTION

The non-ionizing radiation is the radiation which does not have the energy that enables electron to be ionized by tearing electron from atoms and/or molecules; but which has the energy to increase different energy levels by stimulating the electrons of the atoms and/or molecules. Near ultraviolet waves, visible light wave, infrared waves, microwaves or radio waves can be given as examples for the said radiations.

The microwaves interact with the water molecules and enable the said molecules to vibrate in higher speeds and amplitudes. With this feature, the microwaves are also used in heating and cooking.

The devices such as mobile phones, wireless phones, wireless network access points used today operate in microwave band; that is they radiate microwave radiation in are where they are used. Microwave radiations may have adverse effects on living tissues as well as the said radiation may cause adverse effects on operation of devices such as cardiac pacemakers.

In the state of the art, in order to protect the human body from the effects of the non-ionizing radiations, there are accessories such as necklace and the like which enable the said radiation to be absorbed, and which people not wanting to get harmed by the radiations have on them.

International Patent document no WI2012001725, an application known in the state of the art, discloses a device such as ring, earring, brooch, pendant and the like which enables to reduce the effects of the electromagnetic pollution by using graphite powder. Even if the said accessory can provide protection for the person who has it on him/her, it cannot avoid the other interactions that can occur with the said radiations.

SUMMARY OF THE INVENTION

The objective of the present invention is to provide a device for reducing electromagnetic pollution which enables to absorb electromagnetic radiation.

A further objective of the present invention is to provide a device for reducing electromagnetic pollution which enables to decrease interactions that can occur by the environmental radiation by reducing the said radiation level.

DETAILED DESCRIPTION OF THE INVENTION

The device for reducing the electromagnetic pollution developed to fulfill the objectives of the present invention is illustrated in the accompanying figures, in which.

Figure 1:
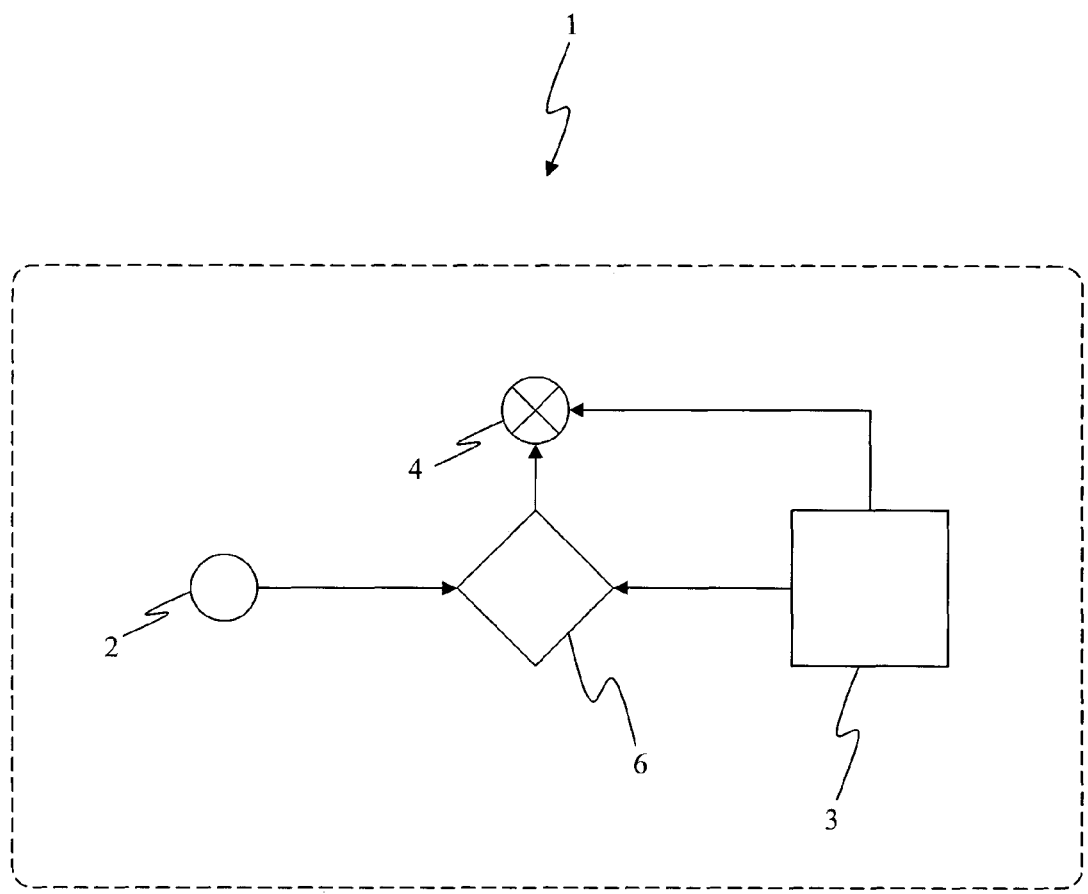
FIG. 1 is the schematic view of one embodiment of the inventive device for reducing the electromagnetic pollution.
Figure 2:
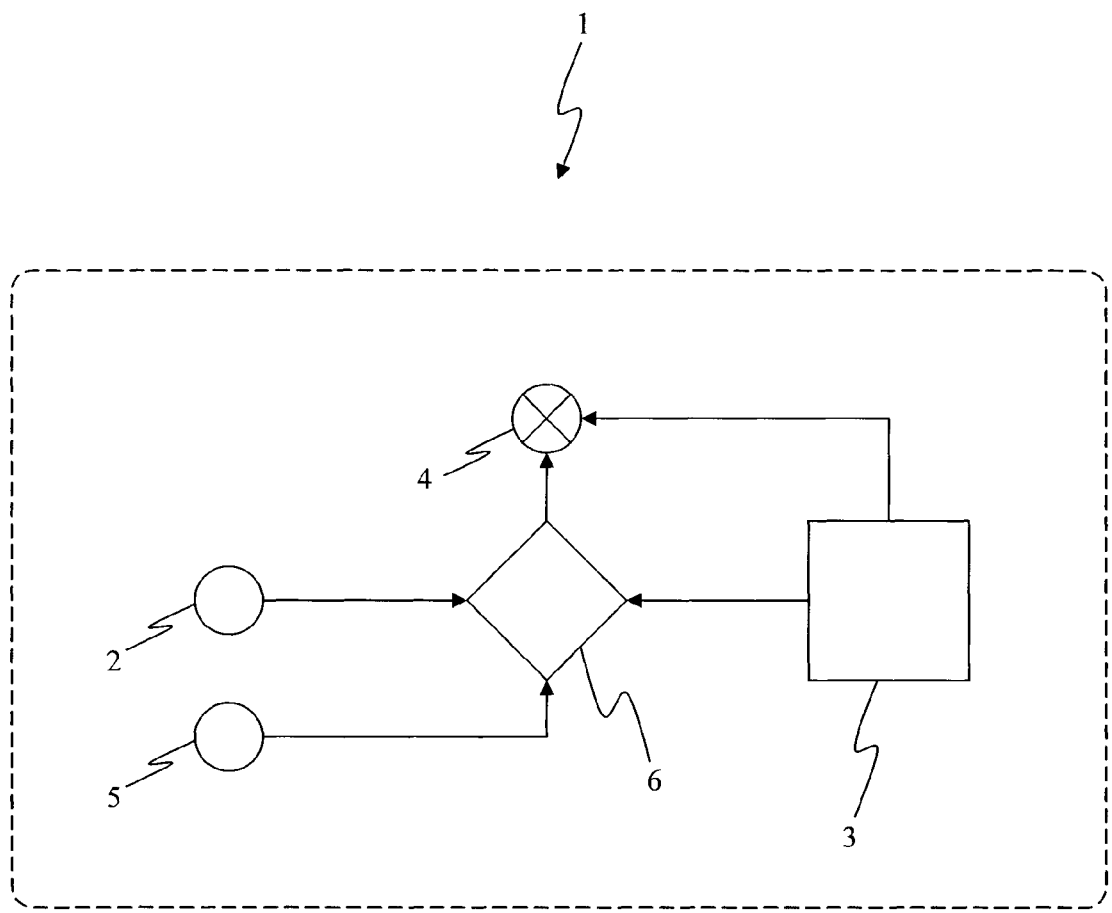
FIG. 2 is the schematic view of another embodiment of the inventive device for reducing the electromagnetic pollution.

The components shown in the figures are each given reference numerals as follows:

1. Device for reducing electromagnetic pollution
2. Sensor
3. Reservoir
4. Valve
5. Level sensor
6. Control unit The inventive device for reducing electromagnetic pollution (1) essentially comprises
  at least one sensor (2) which enables the environmental variables such as non-ionizing radiation level in the environment to be detected,
  at least one reservoir (3) which enables to store the gas to be released to the environment,
  at least one valve (4) which enables the gas present in the reservoir (3) to be released in the environment,
  at least one level sensor (5) which enables the gases in the air such as oxygen to be detected,
  at least one control unit (6) which enables the valve (4) to be controlled in accordance with the information it received from the sensor (2) and the level sensor (5).

In the preferred embodiment of the invention, the sensor (2) detects the non-ionizing radiation level in the environment and informs the control unit (6) about this level. The control unit (6) compares this radiation level with a predetermined threshold level and if the radiation value is bigger than the said threshold value, it enables the valve (4) to be opened for releasing gas into the environment. As a result that the valve (4) is opened, the gas present in the reservoir (3) is released to the environment. Non-ionizing beams are radiated by the said gas molecules and absorbed. Thus the non-ionizing beam density in the environment is reduced. At this moment the sensor (2) continues to measure the radiation level in the environment. When the radiation value measured by the sensor (2) is lower than the predetermined threshold value, the control unit (6) enables the valve (4) to be turned off and thus prevents the gas present in the reservoir (3) from being released to the environment.

In one embodiment of the invention, the inventive device (1) comprises a level sensor (5) which enables to detect the level of gases in the air such as oxygen. The level sensor (5) detects the oxygen in the environment and transmits the said level to the control unit (6). The control unit (6) turns off the valve (4) when the oxygen level in the environment exceeds a predetermined level and thus the oxygen level in the environment is prevented from exceeding a determined level. The control unit (6) also turns the valve (4) on when the oxygen level in the environment is lower than a predetermined level and thus the oxygen level in the environment is prevented from lowering from a determined level.

In the preferred embodiment of the invention, the valve (4) can be a valve such as solenoid valve which has only on/off positions as well as can be a valve the flow rate of which can be changed.

In the preferred embodiment of the invention the gas to be released to the environment is oxygen.

In another embodiment of the invention the gas to be released to the environment is oxygen enriched with thymus extract.

In one embodiment of the invention, the gas to be released to the environment enters into a transmission pipe, which has at least one nozzle thereon, after the gas goes out of the valve (4). Then the gas is released to the environment via the nozzles present on the transmission pipe. Therefore the gas is distributed to the environment homogenously.

It is possible to develop various embodiments of the inventive device for reducing electromagnetic pollution (1). The invention can not be limited to the examples described herein and it is essentially as defined in the claims.

The invention claimed is:

1. A device for reducing electromagnetic pollution comprising:
   at least one sensor, capable of enabling the non-ionizing radiation level in the environment to be detected;
   at least one reservoir capable of enabling to store gas to be released to the environment;
   at least one valve capable of enabling the gas present in the reservoir to be released in the environment and
   at least one control unit capable of enabling the valve to be controlled in accordance with the information received from the sensor.

2. The device for reducing electromagnetic pollution according to claim 1, wherein the control unit is capable of comparing the level of a non-ionizing radiation detected by the sensor with a predetermined threshold level; and in case the radiation value is bigger than the threshold value, enabling the valve to be opened for releasing the gas into the environment.

3. The device for reducing electromagnetic pollution according to claim 1, wherein the control unit is capable of comparing the level of a non-ionizing radiation detected by the sensor with a predetermined threshold level; and in case the radiation value is lower than the threshold value, enabling the valve to be turned off.

4. The device for reducing electromagnetic pollution according to claim 1, further comprising at least one level sensor capable of detecting the level of the gas in the air such as oxygen.

5. The device for reducing electromagnetic pollution according to claim 4, wherein the control unit is capable of comparing the oxygen level detected by the level sensor with a predetermined threshold value; turning the valve on when the oxygen value is lower than the threshold value and thus preventing the oxygen level from lowering than the predetermined level.

6. The device for reducing electromagnetic pollution according to claim 4, wherein the control unit is capable of comparing the oxygen level detected by the level sensor with a predetermined threshold value; turning the valve off when the oxygen value exceeds the threshold value and thus preventing the oxygen level from exceeding the predetermined threshold level.

7. The device for reducing electromagnetic pollution according to claim 4, wherein oxygen is stored in the reservoir.

8. The device for reducing electromagnetic pollution according to claim 4, wherein oxygen enriched with thymus extract is stored in the reservoir.

9. The device for reducing electromagnetic pollution according to claim 4, wherein a transmission pipe is capable of releasing the gas going out of the valve to the environment and enabling the gas to be distributed to the environment homogenously.

10. The device for reducing electromagnetic pollution according to claim 1, wherein a transmission pipe is capable of releasing the gas going out of the valve to the environment and enabling the gas to be distributed to the environment homogenously.

* * * * *